(12) United States Patent
Kang et al.

(10) Patent No.: US 10,758,512 B2
(45) Date of Patent: Sep. 1, 2020

(54) COMPOSITION FOR PREVENTING OR TREATING DISEASE CAUSED BY OVERPRODUCTION OF DIHYDROTESTOSTERONE COMPRISING FUCOXANTHIN

(71) Applicant: KOREA INSTITUTE OF SCIENCE AND TECHNOLOGY, Seoul (KR)

(72) Inventors: Kyungsu Kang, Gangneung-si (KR); Yongsoo Choi, Gangneung-si (KR); Cheol-Ho Pan, Gangneung-si (KR); Sang Min Kim, Seoul (KR); Kwang-Hyun Cha, Gangneung-si (KR); Jin-Chul Kim, Gangneung-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 540 days.

(21) Appl. No.: 15/795,971

(22) Filed: Oct. 27, 2017

(65) Prior Publication Data
US 2018/0116996 A1 May 3, 2018

(30) Foreign Application Priority Data
Oct. 28, 2016 (KR) .................. 10-2016-0142158

(51) Int. Cl.
| | | |
|---|---|---|
| *A61K 36/00* | (2006.01) | |
| *A61K 31/336* | (2006.01) | |
| *A23L 33/105* | (2016.01) | |
| *A61K 36/03* | (2006.01) | |

(52) U.S. Cl.
CPC .......... *A61K 31/336* (2013.01); *A23L 33/105* (2016.08); *A61K 36/03* (2013.01)

(58) Field of Classification Search
CPC ..................................................... A61K 36/00
USPC ........................................................ 424/725
See application file for complete search history.

(56) References Cited

FOREIGN PATENT DOCUMENTS

| | | |
|---|---|---|
| JP | 2012-219027 A | 11/2012 |
| KR | 10-0828068 B1 | 5/2008 |
| WO | WO 2009/048249 A2 | 4/2009 |

OTHER PUBLICATIONS

Azzouni et al., "Role of 5α-reductase inhibitors in benign prostatic diseases", Prostate Cancer and Prostatic Diseases, vol. 15, 2012, pp. 222-230.
Das et al., "Fucoxanthin induces cell cycle arrest at $G_0/G_1$ phase in human colon carcinoma cells throguh up-regulation of $p21^{WAF1/Cip1}$", Biochimica et Biophysica Acta, vol. 1726, 2005, pp. 328-335.
Maeda et al., "Fucoxanthin from edible seaweed, *Undaria pinnatifida*, shows antiobesity effect through UCP1 expression in white adipose tissues", Biochemical and Biophysical Research Communications, vol. 332, 2005, pp. 392-397.
Office Action of Korean Patent Application No. 10-2016-0142158, dated Oct. 13, 2017.
Shiratori et al., "Effects of fucoxanthin on lipopolysaccharide-induced inflammation in vitro and in vivo", Experimental Eye Research, vol. 81, 2005, pp. 422-428.
Sugawara et al., "Antiangiogenic Activity of Brown Algae Fucoxanthin and its Deacetylated Product, Fucoxanthinol", Journal of Agricultural and Food Chemistry, vol. 54, 2006, pp. 9805-9810.
Yim et al., "5α-Reductase inhibitors in androgenetic alopecia", Current Opinion in Endocrinology, Diabetes & Obesity, vol. 21, No. 6, Dec. 2014, pp. 493-498.

*Primary Examiner* — Michael V Meller
(74) *Attorney, Agent, or Firm* — Birch, Stewart, Kolasch & Birch, LLP

(57) ABSTRACT

Provided is a pharmaceutical composition, a health food composition, or a quasi drug composition for preventing, treating, or improving a disease caused by overproduction of dihydrotestosterone, including fucoxanthin or a *Phaeodactylum tricornutum* extract as an active ingredient.

1 Claim, 3 Drawing Sheets

COMPOSITION FOR PREVENTING OR TREATING DISEASE CAUSED BY OVERPRODUCTION OF DIHYDROTESTOSTERONE COMPRISING FUCOXANTHIN

CROSS-REFERENCE TO RELATED APPLICATION

This application claims the benefit of Korean Patent Application No. 10-2016-0142158, filed on Oct. 28, 2016, in the Korean Intellectual Property Office, the disclosure of which is incorporated herein in its entirety by reference.

BACKGROUND

1. Field

The present disclosure relates to a pharmaceutical composition and a health food composition for treating a disease caused by overproduction of dihydrotestosterone (DHT), and more particularly, to a pharmaceutical composition and a health food composition which are effective for treating, preventing, or improving a disease exacerbated by overproduction of dihydrotestosterone (DHT), for example, prostatic hyperplasia, hormone therapy, or male pattern baldness.

2. Description of the Related Art

Testosterone which is a male hormone is an important hormone that maintains masculine characteristics of the body and regulates numerous physiological processes. Testosterone is known to be converted into dihydrotestosterone (DHT) by 5alpha-reductase (5α-reductase) enzyme. It is known that binding affinity of dihydrotestosterone for androgen receptors is about 5 times higher than that of testosterone, and thus the ability of dihydrotestosterone to induce androgen signaling, that is, its male hormone function is about 10 times stronger than that of testosterone. However, overproduction of dihydrotestosterone may cause benign prostatic hyperplasia, leading to urination problems, etc., and it may also promote male pattern baldness (Non-Patent Documents 1 and 2). Thus, these diseases may be controlled by inhibiting dihydrotestosterone production using drugs.

A 5α-reductase inhibitor inhibits conversion of testosterone into dihydrotestosterone, thereby being clinically applied in the treatment of diseases caused by overproduction of dihydrotestosterone. Thus, the 5α-reductase inhibitor may be used in the treatment or improvement of prostatic hyperplasia or male pattern baldness, and a representative drug is finasteride (product name: Propecia, Proscar). It is also known that 5α-reductase inhibitor may be used as a male hormone inhibitor together with estrogen for transgender women. However, when finasteride is administered to men, there are drawbacks that side effects such as erectile dysfunction, ejaculation disorders, low libido, etc. may occur.

Meanwhile, fucoxanthin having a structure of the following Formula 1 is a carotenoid abundant in edible seaweeds such as sea mustard, gulfweed, kelp, hijiki, etc., or a microalgae *Phaeodactylum tricornutum*, and fucoxanthin is known as a safe physiologically active substance found in edible seaweeds, and many studies reported that fucoxanthin has various physiological activities:

[Formula 1]

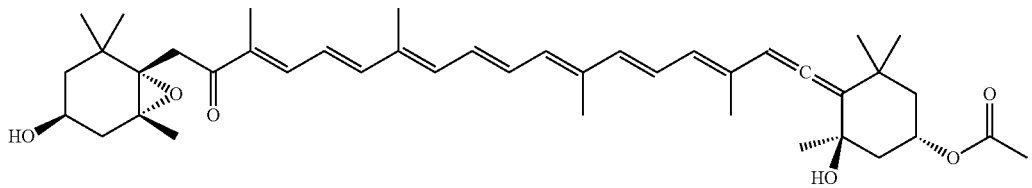

Specifically, it was revealed that fucoxanthin has an anticancer effect (Non-Patent Document 3), an anti-inflammatory effect (Non-Patent Document 4), an angiogenesis-inhibitory effect (Non-Patent Document 5), an anti-obesity effect (Non-Patent Document 6), and a therapeutic effect on hyperlipidemia (Patent Document 1). However, there have been no studies on a dihydrotestosterone production-inhibitory effect of fucoxanthin.

PRIOR ART DOCUMENTS

Patent Documents

1. Korean Patent NO. 0828068

Non-Patent Documents

1. Yim E. et al., "5α-Reductase inhibitors in androgenetic alopecia", Current Opinion in Endocrinology, Diabetes & Obesity, 21:493-498, 2014
2. Azzouni F. and Mohler J., "Role of 5α-reductase inhibitors in benign prostatic diseases", Prostate Cancer Prostatic Diseases 15: 222-230, 2012
3. Das, S. K. et al., "Fucoxanthin induces cell cycle arrest at $G_0/G_1$ phase in human colon carcinoma cells through up-regulation of $p21^{WAF1/Cip1}$", Biochim. Biophys. Acta., 2005, 1726(3):328-335
4. Shiratori, K. et al., "Effects of fucoxanthin on lipopolysaccharide-induced inflammation in vitro and in vivo", Exp Eye Res. 2005, 81(4):422-428
5. Sugawara, T. et al., "Antiangiogenic Activity of Brown Algae Fucoxanthin and its Deacetylated Product, Fucoxanthinol", J. Agric. Food Chem. 2006, 54(26):9805-9810
6. Maeda, H. et al., "Fucoxanthin from edible seaweed, *Undaria pinnatifida*, shows antiobesity effect through UCP1 expression in white adipose tissues", Biochem. Biophys. Res. Commun., 2005, 332(2):392-397)

SUMMARY

Technical Problem

Known synthetic 5α-reductase inhibitors such as finasteride have drawbacks of inducing side effects such as erectile dysfunction, ejaculation disorders, low libido, etc. Accordingly, there is a demand for natural product-derived 5α-reductase inhibitors which may be safely used.

An object of the present disclosure is to provide a pharmaceutical composition including a safe natural product-derived active ingredient having a dihydrotestosterone production-inhibitory effect.

Another object of the present disclosure is to provide a health food composition including a safe natural product-derived active ingredient having a dihydrotestosterone production-inhibitory effect.

Still another object of the present disclosure is to provide a quasi drug composition including a safe natural product-derived active ingredient having a dihydrotestosterone production-inhibitory effect.

Technical Solution

An aspect of the present disclosure provides a pharmaceutical composition for preventing or treating a disease caused by overproduction of dihydrotestosterone, including fucoxanthin of the following Formula 1 or a *Phaeodactylum tricornutum* extract as an active ingredient:

[Formula 1]

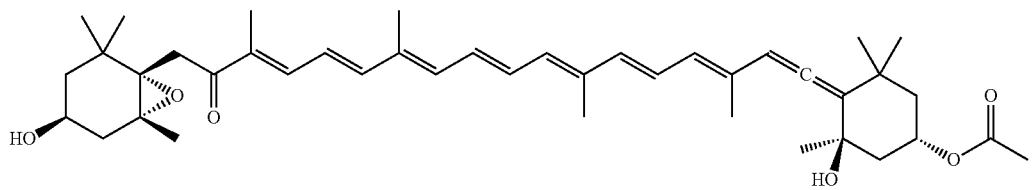

Another aspect of the present disclosure provides a health food composition for preventing or improving a disease caused by overproduction of dihydrotestosterone, including fucoxanthin of the following Formula 1 or a *Phaeodactylum tricornutum* extract as an active ingredient.

Still another aspect of the present disclosure provides a quasi drug composition for preventing or improving a disease caused by overproduction of dihydrotestosterone, including fucoxanthin of the following Formula 1 or a *Phaeodactylum tricornutum* extract as an active ingredient.

Effect of the Invention

A pharmaceutical composition, a health food composition, and a quasi drug composition including fucoxanthin or a *Phaeodactylum tricornutum* extract according to an aspect of the present disclosure may have a dihydrotestosterone production-inhibitory effect, thereby being used for the prevention, improvement, or treatment of a disease caused by overproduction of dihydrotestosterone. In addition, the compositions have advantages of being safely used without side effects, because they include a safe natural product-derived ingredient.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
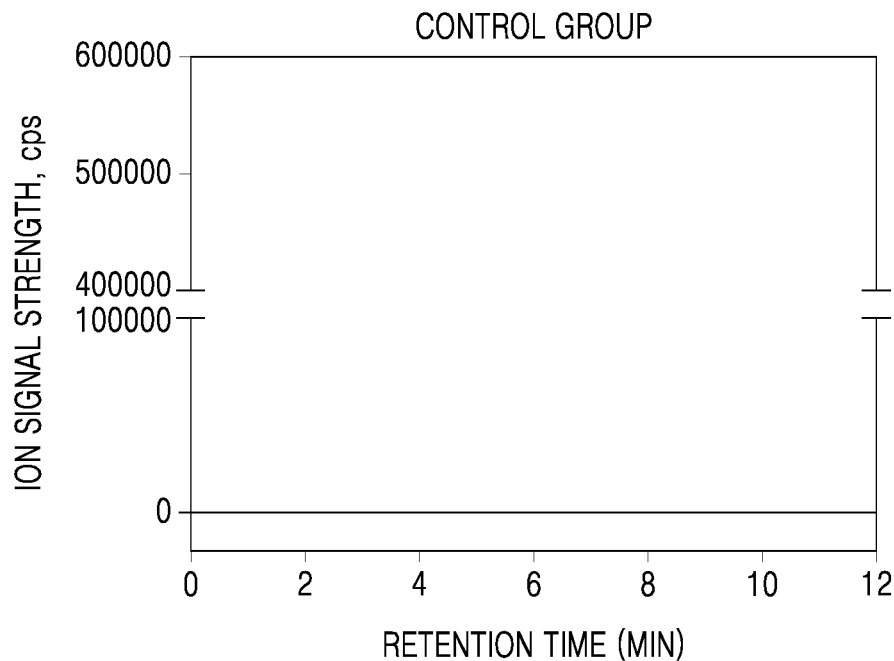
FIG. 1A is a graph showing ion signal strength of LC-MS/MS spectrum detecting testosterone and dihydrotestosterone in a control group treated with no testosterone and FIG. 1B is a graph showing ion signal strength of LC-MS/MS spectrum detecting testosterone and dihydrotestosterone in a prostate cell line DU145 treated with testosterone (100 ng/mL)

Hereinafter, the present disclosure will be described in more detail.

All technical terminologies used herein, unless defined otherwise, may be understood as having the same meanings known to one of ordinary skilled in the related art. In addition, although desired methods or samples are introduced in the present specification, methods and samples similar or equivalent thereto may also be included in the scope of the present invention. All references referred to in the present specification may be incorporated herein by reference.

The present inventors have conducted studies to find a safe natural product-derived ingredient having a dihydrotestosterone production-inhibitory effect. As a result, it was demonstrated that fucoxanthin known as a safe physiologically active material has excellent dihydrotestosterone production-inhibitory activity. Specifically, high-purity fucoxanthin was obtained from *Phaeodactylum tricornutum*, and the dihydrotestosterone production-inhibitory activity thereof was measured. As a result, the dihydrotestosterone production-inhibitory effect was clearly observed. Accordingly, fucoxanthin and a *Phaeodactylum tricornutum* extract may be used in the prevention, improvement, and treatment of a disease caused by overproduction of dihydrotestosterone.

An aspect of the present invention provides a pharmaceutical composition for preventing or treating a disease caused by overproduction of dihydrotestosterone, including fucoxanthin of the following Formula 1 or a *Phaeodactylum tricornutum* extract as an active ingredient:

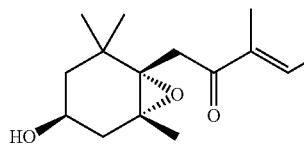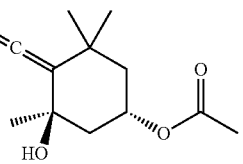

[Formula 1]

Another aspect of the present invention provides a health food composition for preventing or improving a disease caused by overproduction of dihydrotestosterone, including fucoxanthin of the following Formula 1 or a *Phaeodactylum tricornutum* extract as an active ingredient.

Still another aspect of the present invention provides a quasi drug composition for preventing or improving a disease caused by overproduction of dihydrotestosterone, including fucoxanthin of the following Formula 1 or a *Phaeodactylum tricornutum* extract as an active ingredient.

As used herein, the "disease caused by overproduction of dihydrotestosterone" refers to any disease that may be exacerbated by abnormal overproduction of dihydrotestosterone and may be prevented, improved, or treated by inhibiting production of dihydrotestosterone, and may be known or found in future, and the disease includes prostatic hyperplasia, male pattern baldness, and hormone replacement therapy for transgender women, but is not limited thereto.

As used herein, the "hormone replacement therapy for transgender women" refers to a therapy of administering any drug which is used for femininity development after male-to-female gender reassignment surgery, but also include administration of any drug for increasing femininity of a person who is innately a man although he has not gender reassignment surgery.

As used herein, the term "health food" refers to a food good for health in the ordinary acceptation, and a "health functional food" is a sub-concept of health food, which is recognized as a functional and safe food by the government through a thorough authentication process, and refers to a health functional food containing ingredients that are on the authorized list of ingredients according to the Korean Food and Drug Administration Announcement #2008-72, and their functionality and safety are established by the Health Functional Food Act amended in 2008.

As used herein, the term "quasi drug" refers to non-appliance or non-machinery articles that have insignificant influences on or do not directly act upon human bodies.

Hereinafter, the pharmaceutical composition, the health food composition, and the quasi drug composition according to the present disclosure are comprehensively referred to as "composition of the present disclosure".

Fucoxanthin is a physiologically active material which is known to exist in a brown algae, for example, sea mustard, kelp, gulfweed, hijiki, etc., as well as in a microalgae *Phaeodactylum tricornutum*. Therefore, fucoxanthin in the composition may be obtained from any known natural product including fucoxanthin, or commercially available fucoxanthin may be purchased and used. In a specific embodiment, the fucoxanthin is fucoxanthin derived from *Phaeodactylum tricornutum*.

In a specific embodiment, the composition according to the present disclosure may include fucoxanthin as a *Phaeodactylum tricornutum* extract. The *Phaeodactylum tricornutum* extract may be an extract prepared by any known method capable of extracting fucoxanthin. The *Phaeodactylum tricornutum* extract may be a C1-C3 alcohol extract of *Phaeodactylum tricornutum*, specifically, an ethanol extract, and more specifically, a 100% ethanol extract. Preferably, the composition according to the present disclosure may include high-purity fucoxanthin by further purifying the *Phaeodactylum tricornutum* extract.

In a specific embodiment, the high-purity fucoxanthin may be obtained by purifying the 100% ethanol extract of *Phaeodactylum tricornutum* by silica gel chromatography.

An experimental result showed that when prostate cells were treated with high-purity fucoxanthin obtained from the *Phaeodactylum tricornutum* extract, together with testosterone, dihydrotestosterone production was decreased, as compared with a negative control group treated with testosterone alone, and dihydrotestosterone production was markedly decreased with increasing concentration of the treated fucoxanthin (Experimental Example 1). Therefore, it was confirmed that the *Phaeodactylum tricornutum* extract and fucoxanthin included in the composition according to the present disclosure have a remarkable dihydrotestosterone production-inhibitory effect.

Further, in order to examine whether the dihydrotestosterone production-inhibitory effect of fucoxanthin is attributed to a prostate cell-killing effect due to cytotoxicity of fucoxanthin, cell viability of prostate cells was tested. As a result, it was confirmed that fucoxanthin did not influence cell viability of prostate cells, like a positive control drug, finasteride (Experimental Example 2). Therefore, it was confirmed that the *Phaeodactylum tricornutum* extract and fucoxanthin included in the composition according to the present disclosure have a remarkable dihydrotestosterone production-inhibitory effect without showing the cell killing affect on prostate cells.

Since the composition according to the present disclosure has the remarkable dihydrotestosterone production-inhibitory effect without showing the cell killing affect on prostate cells, it may be effectively used in the prevention, improvement, or treatment of any disease caused by overproduction of dihydrotestosterone. Further, since the composition according to the present disclosure includes fucoxanthin which is an active ingredient derived from a safe natural product used commonly, there is an advantage that the risk of side effects due to a known synthetic drug, finasteride is remarkably low.

In a specific embodiment, a content of the fucoxanthin or the *Phaeodactylum tricornutum* extract in the pharmaceutical composition may be appropriately determined by purpose of use (prevention or improvement). Generally, fucoxanthin may be included in an amount of 0.01% by weight to 10% by weight, based on the total weight of the pharmaceutical composition.

The pharmaceutical composition may be appropriately formulated by using a pharmaceutically acceptable carrier together with the fucoxanthin or the *Phaeodactylum tricornutum* extract. The pharmaceutical composition may include an oral formulation, an injectable formulation, a suppository, a percutaneous formulation, and a nasal formulation, but the pharmaceutical composition may be prepared into any formulation not limited thereto. Preferably, the pharmaceutical composition may be prepared into an oral formulation such as a liquid, a suspension, a powder, a granule, a tablet, a capsule, a pill, or an extract.

Upon preparation into such formulations, a pharmaceutically acceptable carrier or additive required for the preparation of each formulation may be added. Upon preparation into an oral formulation, one or more selected from a diluent, a lubricant, a binder, a disintegrating agent, a sweetening agent, a stabilizing agent, and a preservative may be used as the carrier, and one or more selected from a flavoring agent, vitamins, and an antioxidant may be used as the additive.

The carriers and additives may be any pharmaceutically acceptable example. In a specific embodiment, lactose, corn starch, soybean oil, microcrystalline cellulose, or mannitol may be used as the diluent, magnesium stearate or talc may be used as the lubricant, and polyvinylpyrrolidone or hydroxypropyl cellulose may be used as the binder. In addition, calcium carboxymethyl cellulose, sodium starch glycolate, potassium polyacrylate, or crospovidone may be used as the disintegrating agent, white sugar, fructose, sorbitol or aspartame may be used as the sweetening agent, sodium carboxymethylcellulose, beta-cyclodextrin, white bee's wax, or Xhantan gum may be used as the stabilizing agent, and methyl parahydroxybenzoate, propyl parahydroxybenzoate, or potassium sorbate may be used as the preservative.

In addition to these ingredients, known additives for improving flavor, for example, a natural flavoring agent such as plum, lemon, pineapple or herb flavor, a natural fruit juice, a natural dye such as chlorophyllin or flavonoid, a sweetening component such as fructose, honey, sugar alcohol, or sugar, or an acidulant such as citric acid or sodium citrate may also be included.

The pharmaceutical composition may be parenterally or orally administered as desired. Upon parenteral administration, fucoxanthin may be administered at a daily dose of 0.01 mg to 100 mg per 1 kg of body weight, and more specifically, at a daily dose of 0.1 mg to 50 mg per 1 kg of body weight, and upon oral administration, fucoxanthin may be administered at a daily dose of 0.01 mg to 1000 mg per 1 kg of body weight, and more specifically, at a daily dose of 0.1 mg to 300 mg per 1 kg of body weight, once to several times. It should be understood that an administration dose for a particular patient may be determined by various related factors such as the patient's body weight, age, gender, health conditions, diet, an administration time, an administration method, severity of disease, etc., and the administration dose is not limited to the scope of the present disclosure in any aspect.

A content of the fucoxanthin or *Phaeodactylum tricornutum* extract in the health food composition according to the present disclosure may be, is not particularly limited to, about 0.01% by weight to about 10% by weight, based on the composition in the health food composition.

In a specific embodiment, a content of the fucoxanthin or the *Phaeodactylum tricornutum* extract in the health food composition may be appropriately determined by purpose of use (prevention or improvement). Generally, the fucoxanthin or the *Phaeodactylum tricornutum* extract may be included in an amount of 0.01% by weight to 8% by weight, based on the total weight of the food composition. When the health food composition is prepared as a drink, the fucoxanthin or the *Phaeodactylum tricornutum* extract may be included in an amount of 0.02 g to 8 g, and preferably 0.3 g to 1 g, based on 100 mL.

An administration dose of the health food composition is not particularly limited, but fucoxanthin may be administered several times such that a total daily dose is about 0.01 mg/kg to about 1000 mg/kg per adult. The administration dose may vary depending on progression of a disease, an administration route, gender, age, body weight, purpose of use (prevention or treatment), etc., and may be added or subtracted according to a professional's decision.

The health food composition may be prepared into a general formulation, for example, a powder, a granule, a tablet, a pill, a capsule, a suspension, an emulsion, a syrup, an infusion, a liquid, or an extract, and prepared into any health food such as meats, sausages, bread, chocolate, candies, snacks, cookies, pizzas, instant noodles, other noodles, chewing gums, jelly, dairy products including ice cream, various soups, beverages, teas, drinks, alcoholic drinks, vitamin complexes, etc. For formulation of the health food, a carrier or an additive acceptable in sitology may be used, and any carrier or additive which is known in the art to be applicable in the formulation to be prepared may be used.

The additive may include a variety of nutrients, vitamins, electrolytes, flavoring agents, coloring agents, pectic acid and salts thereof, alginic acid and salts thereof, organic acids, protective colloidal thickeners, pH adjusters, stabilizers, preservatives, glycerin, alcohols, carbonating agents used in carbonated beverage. In addition, the health food composition may include natural fruit juices and fruit pulps for the preparation of fruit juice drinks and vegetable drinks. These additive ingredients may be used independently or in combination. A proportion of the additive is not critical, but may be selected from 0.01 parts by weight to 0.1 parts by weight, based on 100 parts by weight of the health food composition.

The beverage may further include other ingredients in addition to the above-described active ingredient, and may further include a variety of flavoring agents or natural carbohydrates commonly used in beverages. Examples of the natural carbohydrates are common sugars such as monosaccharide (e.g., glucose, fructose, etc.), disaccharide (e.g., maltose, sucrose, etc.), and polysaccharide (e.g., dextrin, cyclodextrin, etc.), and sugar alcohol such as xylitol, sorbitol, erythritol, etc. As the other flavoring agent, a natural flavoring agent (e.g., taumatin, *stevia* extract, etc.) and a synthetic flavoring agent (e.g., saccharin, aspartame, etc.) may be included. It is preferable that the natural carbohydrate is generally included in an amount of about 1 g to about 20 g, preferably about 5 to about 12 g, based on 100 ml of the beverage.

In a specific embodiment, the health food may be a health functional food composition.

The quasi drug composition according to the present disclosure may be prepared in any type of quasi drug known in the art. For example, the quasi drug composition may be a quasi drug selected from the group consisting of shampoos, conditioners, soaps, ointments, cosmetics, hair care products, skin care products, hair gels, sprays, and perfumes, but is not limited thereto.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

Hereinafter, the present invention will be described in more detail with reference to Examples. However, these Examples are for illustrative purposes only, and the invention is not intended to be limited by these Examples.

Example 1. Separation of High-Purity Fucoxanthin from Microalgae 20 g of *Phaeodactylum tricornutum* powder which was a freeze-dried microalgae was extracted by sonication using a 100% ethanol solvent at room temperature for 3 hours. The powder was filtered out of the extract solution by using a filter paper (3M), and the solvent was removed by a vacuum evaporator to obtain 3 g of a final *Phaeodactylum tricornutum* extract. A high-purity fucoxanthin was separated from the extract by using Silica-column chromatography. A glass column having a diameter of 2 cm and a length of 30 cm was packed with silica gel of 63 mesh-200 mesh, and then chromatography of the *Phaeodactylum tricornutum* extract was performed under a mobile phase solvent of n-hexane: acetone (7:3). Fucoxanthin bands of dark red color were collected in a 10 mL-test tube to obtain respective fraction solutions while flowing the mobile phase solvent under dark conditions. Each of the test tubes was analyzed by HPLC to examine the presence or absence of fucoxanthin, and the test tubes including only fucoxanthin were collected and concentrated under vacuum to obtain 33 mg of high-purity fucoxanthin. The obtained fucoxanthin was analyzed by $^1$H and $^{13}$C NMR, confirming that the fucoxanthin has an all-trans fucoxanthin structure of Formula 1 and purity of 95% or higher. $^1$H and $^{13}$C NMR spectrum data of fucoxanthin are the same as in the following Table 1.

Experimental Example 1. Measurement of Dihydrotestosterone Production-Inhibitory Activity in Prostate Cells Concentrations of testosterone and dihydrotestosterone in prostate cells were measured by LC-MS/MS to identify dihydrotestosterone production-inhibitory activity of high-purity fucoxanthin of Example 1 in prostate cells.

[Sample Purchase]

Testosterone, dihydrotestosterone, and dimethyl sulfoxide were purchased from Sigma Aldrich. HPLC grade water, methanol, and acetonitrile solvents were purchased from Fisher Scientific Company. As an internal standard, 2-(1-(4-chlorobenzoyl)-5-methoxy-2-methyl-1H-indol-3-yl)acetic acid was used.

[Cell Culture]

CWR-22Rv1, LNCaP, DU145, and PC-3 cells which are human prostate cancer cell lines were cultured and maintained in an RPMI medium (Roswell Park Memorial Institute medium) supplemented with 10% heat-inactivated fetal bovine serum (FBS), 10 U/mL penicillin, and 100 μg/mL streptomycin under conditions of 5% carbon dioxide and 37° C.

[LC-MS/MS Technique]

The internal standard compound was dissolved in dimethyl sulfoxide at a concentration of 10 μM, and 1 μL thereof was added to 150 μL of cell culture, and treated to a cartridge to perform sample pretreatment. The cartridge used herein was a strata X polymer-based cartridge (a particle size of 33 μm) of Phenomenex company, and testosterone, dihydrotestosterone, and internal standard compound to be analyzed were extracted with 500 μL of methanol twice, and dried by a vacuum centrifuge (Thermo Savant SPD1010, Holbrook, N.Y., USA). Thereafter, re-solvation was performed by using 50% aqueous methanol, and products were kept frozen at −20° C.

Mass spectrometry of the stored samples was performed by using an AB SCIEX API 4000 QTRAP tandem quadrupole mass spectrometer. HPLC system used herein was

TABLE 1

NMR spectrum data of high-purity fucoxanthin isolated from microalgae *Phaeodactylum tricornutum*

| Position | $^{13}$C(125 Mhz) | $^1$H (multiplicity, J = Hz, 500 Mhz) | Position | $^{13}$C(125 Mhz) | $^1$H (multiplicity, J = Hz, 500 Mhz) |
|---|---|---|---|---|---|
| 1 | 34.95 |  | 1' | 35.31 |  |
| 2 | 47.27 | 1.50 (1H, d, m) | 2' | 45.26 | 1.99 (1H, m) |
|  | 47.27 | 1.28 (1H, m) |  | 45.26 | 1.41 (1H, m) |
| 3 | 63.00 | 3.70 (1H, d, m) | 3' | 67.83 | 5.40 (1H, dd, J = 9.52, 13.70) |
| 4 | 41.12 | 1.72 (1H, dd, J = 10.72, 13.71) | 4' | 45.14 | 1.51 (1H, m) |
|  | 41.12 | 2.28 (1H, d, t = 7.44, 7.44) |  | 45.14 | 2.23 (1H, m) |
| 5 | 66.43 |  | 5' | 71.43 |  |
| 6 | 67.45 |  | 6' | 116.73 |  |
| 7 | 40.29 | 2.63 (1H, d, J = 18.60) | 7' | 202.23 |  |
|  | 40.29 | 3.85 (1H, d, J = 18.62) |  |  |  |
| 8 | 199.65 |  | 8' | 102.82 | 6.11 (1H, s) |
| 9 | 133.73 |  | 9' | 132.19 |  |
| 10 | 139.88 | 7.37 (1H, d, J = 11.01) | 10' | 128.34 | 6.17 (1H, d, J = 11.38) |
| 11 | 123.23 | 6.71 (1H, d, J = 10.76) | 11' | 125.43 | 6.69 (1H, m) |
| 12 | 145.38 | 6.86 (1H, d, J = 14.74) | 12' | 137.10 | 6.41 (1H, d, J = 14.95) |
| 13 | 135.35 |  | 13' | 137.73 |  |
| 14 | 136.69 | 6.53 (1H, d, J = 11.58) | 14' | 132.10 | 6.33 (1H, d, J = 11.58) |
| 15 | 129.19 | 6.73 (1H, m) | 15' | 132.39 | 6.85 (1H, t, J = 12.75, 12.75) |
| 16 | 23.47 | 1.05 (3H, s) | 16' | 31.22 | 1.10 (3H, s) |
| 17 | 27.18 | 0.96 (3H, s) | 17' | 29.39 | 1.31 (3H, s) |
| 18 | 19.80 | 1.22 (3H, s) | 18' | 28.01 | 1.40 (3H, s) |
| 19 | 10.34 | 1.95 (3H, s) | 19' | 12.86 | 1.86 (3H, s) |
| 20 | 11.29 | 2.03 (3H, s) | 20' | 11.46 | 2.02 (3H, s) |
|  |  |  | 21' | 170.90 |  |
|  |  |  | 22' | 19.80 | 2.05 (3H, s) |

Agilent 1200 pump, and solvent A was water/acetonitrile (95:5 v/v, 0.1% formic acid), and solvent B was acetonitrile/water (95:5 v/v, 0.1% formic acid). For chromatography separation, a linear gradient from 40% B solvent to 100% B solvent in 8 minutes was used. An analysis column used herein was an XTerra MS C18 column (2.1 mm×150 mm, 3.5 μm) of Waters corporation, and analysis was performed while maintaining temperature at 25° C. and a flow rate of 0.2 mL/min. Tandem mass spectra were obtained by positive ionization, and an ionization voltage was 5500 V and an ionization temperature was 400° C. Further, ultra high-purity nitrogen gas (99.999% purity) was applied to curtain gas, GS1 gas, and GS2 gas, respectively. In this regard, values of the used gases were set at 30, 35, and 40, respectively. Further, mass spectrometry was performed under optimized ion conditions for respective analytes as in the following Table 2.

TABLE 2

Tandem mass fragmentation m/z values and ion guide values of optimal conditions for analysis of testosterone, dihydrotestosterone, and internal standard compound

| Compound | SRM value (m/z) | DP (eV) | EP (eV) | CE (eV) | CXP (eV) |
|---|---|---|---|---|---|
| Testosterone | 289/97 | 96 | 10 | 33 | 16 |
| Dihydrotestosterone | 291/255 | 101 | 10 | 23 | 14 |
| Internal standard compound | 358/139 | 71 | 10 | 25 | 10 |

[Measurement of Dihydrotestosterone-Inhibitory Activity and Result]

With regard to CWR-22Rv1, LNCaP, DU145, and PC-3 cells which are human prostate cancer cell lines cultured and maintained as above, the culture medium and prostate cell culture were mixed, and $1 \times 10^4$ cells were seeded in a 96-well plate, and then cultured for 24 hours under conditions of 5% carbon dioxide and 37° C.

After being stabilized, the cells were treated with only 0.2% dimethyl sulfoxide as a control group, treated with testosterone (100 ng/mL or 200 ng/mL) alone, or treated with testosterone and 10 μM finasteride as a positive control or testosterone and 1 μM, 10 μM, or 20 μM fucoxanthin, and then cultured for 48 hours. Thereafter, media were collected for LC-MS/MS analysis, and subjected to the above pre-treatment, and then used in LC-MS/MS analysis.

Figure 1B:
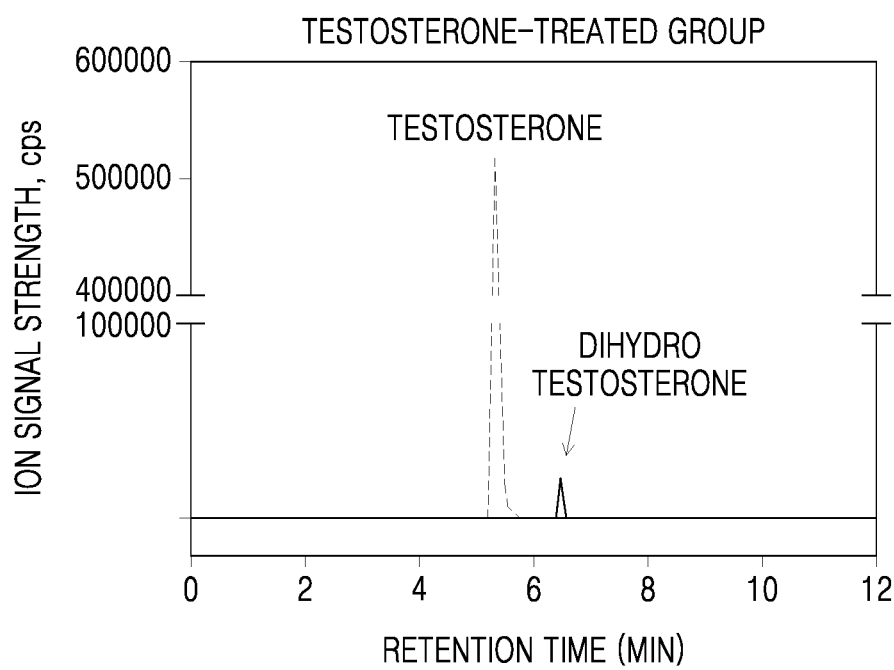

DU145 prostate cells were treated with 100 ng/mL of testosterone, and then testosterone and dihydrotestosterone were measured. Results are shown in FIGS. 1A and 1B. According to ion signal strength of the LC-MS/MS spectrum of FIGS. 1A and 1B, together with residual testosterone, dihydrotestosterone was found to be produced.

Figure 2:
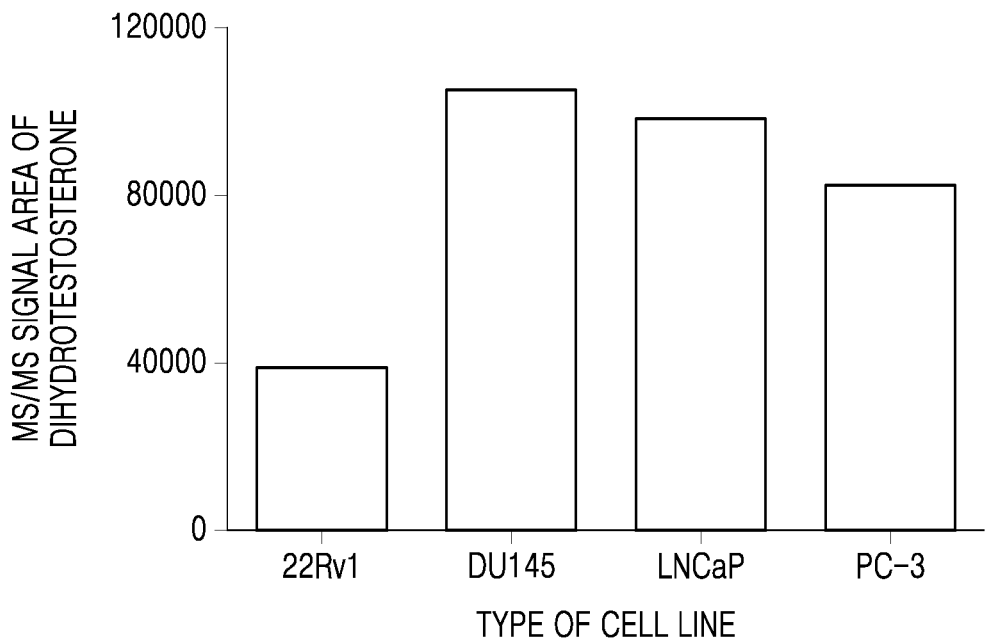
FIG. 2 is a graph showing production amounts of dihydrotestosterone which was produced in various prostate cell lines, CWR-22Rv1, LNCaP, DU145, and PC-3 by treatment of testosterone (200 ng/mL)

Further, in addition to DU145, various prostate cell lines, CWR-22Rv1, LNCaP, and PC-3 were treated with 200 ng/mL of testosterone, and then LC-MS/MS technique was used to measure testosterone and dihydrotestosterone. Results are shown in FIG. 2. According to FIG. 2, all prostate cell lines experimented were found to produce dihydrotestosterone upon treatment of testosterone. Of them, DU145 showed the highest production of dihydrotestosterone.

Figure 3:
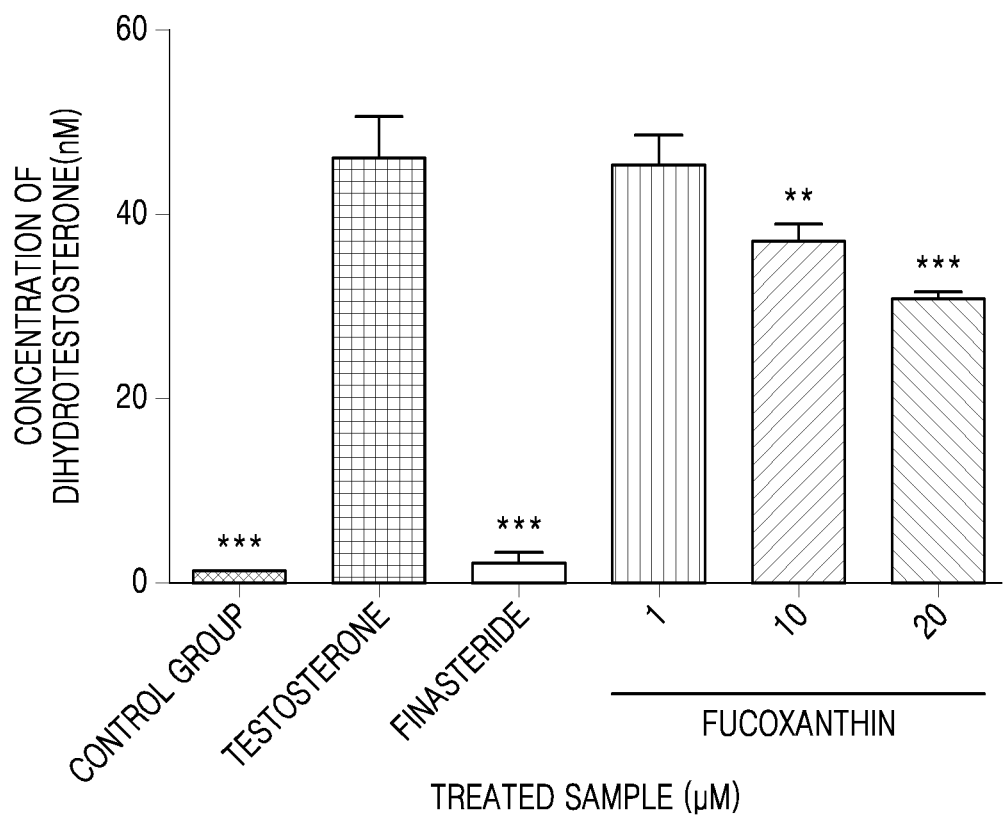
FIG. 3 is a graph showing result of measuring a dihydrotestosterone concentration in a prostate cell line DU145 after treatment of testosterone (100 ng/mL) and finasteride (10 μM) or fucoxanthin (1 μM, 10 μM, or 20 μM)

Therefore, the prostate cell DU145 was used in a subsequent experiment for examining the dihydrotestosterone production-inhibitory effect of fucoxanthin, and results are shown in FIG. 3.

According to FIG. 3, a sufficient amount (about 45 nM) of dihydrotestosterone was produced in the prostate cell DU145 by treatment of testosterone. At this time, dihydrotestosterone production was remarkably inhibited by treatment of the positive control drug, finasteride. Dihydrotestosterone production was also remarkably inhibited by treatment of high-purity fucoxanthin (1 μM, 10 μM, 20 μM) of Example 1, and the inhibition was remarkably increased with increasing concentration of fucoxanthin. Therefore, it was revealed that fucoxanthin exhibits a remarkable dihydrotestosterone production-inhibitory effect on prostate cells. The measurement result of each sample was compared with the group treated with testosterone alone by analysis of variance (ANOVA) and Dunnett's test (*$P<0.001$, $P<0.01$).

Experimental Example 2. Evaluation of Cell Viability of Human Prostate Cell Line In order to examine whether the dihydrotestosterone production-inhibitory effect of Experimental Example 1 is attributed to cytotoxicity of the compound itself, cell viability of prostate cells was tested.

With regard to the human prostate cancer cell line DU145 cultured and maintained in Experimental Example 1, the culture medium and prostate cell culture were mixed, and $1 \times 10^4$ cells were seeded in a 96-well plate, and then cultured for 24 hours under conditions of 5% carbon dioxide and 37° C.

After being stabilized, the cells were treated with only 0.2% dimethyl sulfoxide as a control group, treated with testosterone (100 ng/mL or 200 ng/mL) alone, or treated with testosterone and 10 μM finasteride as a positive control, or testosterone and 1 μM, 10 μM, or 20 μM fucoxanthin, and then cultured for 48 hours.

Thereafter, the media were collected for LC-MS/MS analysis, and then cell viability of prostate cells was measured in order to examine whether treatment of the compound influences growth of the prostate cells. The cell viability was determined by measuring absorbance at 450 nm after adding an EZCytox reagent (Daeil Lab Service, Korea) and culturing for 1-4 hours under conditions of 5% carbon dioxide and 37° C. The cell viability was calculated as a percentage relative to cell viability of the control group treated with dimethyl sulfoxide (DMSO) only. The result of measuring cell viability of prostate cells is shown in FIG. 4.

Figure 4:
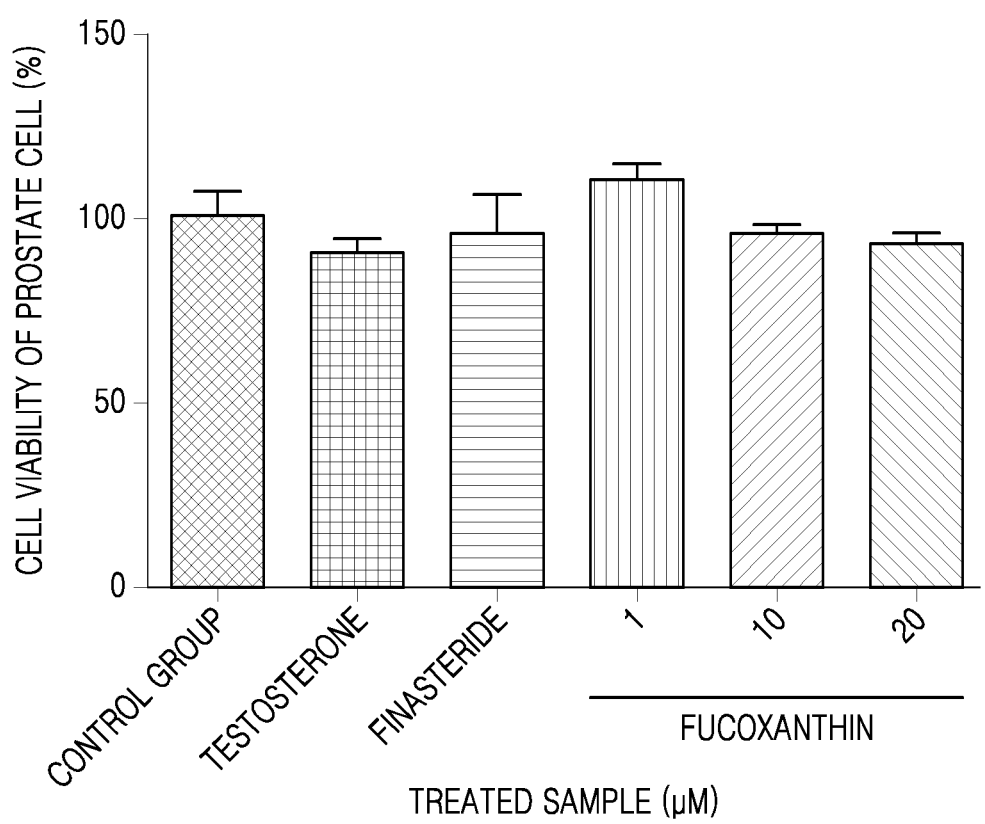
FIG. 4 is a graph showing result of measuring cell viability of a prostate cell line DU145 after treatment of testosterone (100 ng/mL) and finasteride (10 μM) or fucoxanthin (1 μM, 10 μM, or 20 μM).

According to FIG. 4, it was found that finasteride and fucoxanthin did not influence cell viability of prostate cells. Consequently, it can be seen that the dihydrotestosterone production-inhibitory effect of fucoxanthin is attributed not to inhibition of prostate cell survival but to 5α-reductase activity-inhibitory effect. As compared with the non-treated group by analysis of variance (ANOVA) and Dunnett's test, prostate cell growth was not inhibited under any treatment conditions of the compound.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. An emulsion, tablet, pill, chewing gum, sausage, bread, pizza, or capsule consisting essentially of an extract of *Phaeodactylum tricornutum*, crospovidone and hydroxypropyl cellulose.

* * * * *